(12) United States Patent
Yalamanchili

(10) Patent No.: US 9,962,288 B2
(45) Date of Patent: May 8, 2018

(54) ACTIVE ACOUSTIC STREAMING IN HAND PIECE FOR OCCLUSION SURGE MITIGATION

(71) Applicant: Alcon Research, Ltd., Fort Worth, TX (US)

(72) Inventor: Satish Yalamanchili, Irvine, CA (US)

(73) Assignee: Novartis AG (CH)

( * ) Notice: Subject to any disclaimer, the term of this patent is extended or adjusted under 35 U.S.C. 154(b) by 439 days.

(21) Appl. No.: 14/190,652

(22) Filed: Feb. 26, 2014

(65) Prior Publication Data

US 2014/0257172 A1   Sep. 11, 2014

Related U.S. Application Data

(60) Provisional application No. 61/774,359, filed on Mar. 7, 2013.

(51) Int. Cl.
  *A61F 9/007*     (2006.01)
  *A61M 3/02*      (2006.01)
  *A61M 1/00*      (2006.01)

(52) U.S. Cl.
  CPC ...... *A61F 9/00745* (2013.01); *A61F 9/00736* (2013.01); *A61F 9/00763* (2013.01); *A61M 1/0031* (2013.01); *A61M 1/0058* (2013.01); *A61M 1/0064* (2013.01); *A61M 3/0283* (2013.01); *A61M 1/0033* (2014.02); *A61M 2210/0612* (2013.01)

(58) Field of Classification Search
  CPC ............. A61F 9/00736; A61F 9/00745; A61F 9/00763; A61M 1/0031; A61M 1/0033; A61M 1/0058; A61M 1/0064; A61M 2210/0612; A61M 3/0283

See application file for complete search history.

(56) References Cited

U.S. PATENT DOCUMENTS

| | | | |
|---|---|---|---|
| 1,121,697 | A | 12/1871 | Wheatland |
| 2,294,334 | A | 2/1884  | Reed et al. |
| 351,159   | A | 10/1886 | Brengel |
| 863,631   | A | 9/1907  | Cotter |
| 1,061,142 | A | 5/1913  | Tesla |

(Continued)

FOREIGN PATENT DOCUMENTS

| | | |
|---|---|---|
| CA | 2316640     | 2/2001 |
| CA | 2649867 A1  | 6/2001 |

(Continued)

OTHER PUBLICATIONS

International Search Report for PCT/US2010/058931, filed Dec. 3, 2010, Publication No. 2011071775, Published Jun. 16, 2011, 2 pages.

(Continued)

*Primary Examiner* — Imani Hayman

(57) ABSTRACT

An acoustic streaming arrangement supplements irrigation flow to a surgical site. The acoustic streaming arrangement may include an irrigation conduit configured to carry an irrigation fluid to a surgical site, a selectively vibrating flow generator having a sharp edge, and a driving device configured to selectively vibrate the flow generator to create a streaming fluid flow in a direction away from the sharp edge through the irrigation conduit. Systems and methods are also disclosed.

14 Claims, 8 Drawing Sheets

(56) References Cited

U.S. PATENT DOCUMENTS

| | | |
|---|---|---|
| 1,061,206 A | 5/1913 | Tesla |
| 1,874,667 A | 8/1932 | Wada |
| 2,015,123 A | 9/1935 | Pennell |
| 2,121,936 A | 6/1938 | Thomas |
| 2,386,765 A | 10/1945 | Eichelberger |
| 2,536,836 A | 1/1951 | Bowling |
| 2,623,725 A | 12/1952 | Sands |
| 2,755,816 A | 7/1956 | Collins |
| 2,987,004 A | 6/1961 | Murray |
| 3,085,589 A | 4/1963 | Sands |
| 3,191,807 A | 6/1965 | Rodrigues, Jr. |
| 3,336,942 A | 8/1967 | Keith |
| 3,447,478 A | 6/1969 | Clemens |
| 3,487,784 A | 1/1970 | Rafferty et al. |
| 3,561,471 A | 2/1971 | Sands |
| 3,567,345 A | 3/1971 | Ballentine |
| 3,589,363 A | 6/1971 | Banko et al. |
| 3,693,613 A | 9/1972 | Kelman |
| 3,724,974 A | 4/1973 | Molimard |
| 3,756,270 A | 9/1973 | Gibbon |
| 3,784,323 A | 1/1974 | Sausse |
| 3,818,913 A | 6/1974 | Wallach |
| 3,882,872 A | 5/1975 | Dinkelkamp |
| 3,930,505 A | 1/1976 | Wallach |
| 3,996,935 A | 12/1976 | Banko |
| 4,140,118 A | 2/1979 | Jassawalla |
| 4,187,057 A | 2/1980 | Xanthopoulos |
| 4,205,948 A | 6/1980 | Jones |
| 4,255,081 A | 3/1981 | Oklejas et al. |
| 4,392,794 A | 7/1983 | Foxcroft |
| 4,405,289 A | 9/1983 | Nakashima |
| 4,479,761 A | 10/1984 | Bilstad et al. |
| 4,493,706 A | 1/1985 | Borsanyi et al. |
| 4,496,342 A | 1/1985 | Banko |
| 4,530,647 A | 7/1985 | Uno |
| 4,537,561 A | 8/1985 | Xanthopoulos |
| 4,657,490 A | 4/1987 | Abbott |
| 4,661,093 A | 4/1987 | Beck et al. |
| 4,684,328 A | 8/1987 | Murphy |
| 4,705,500 A | 11/1987 | Reimels et al. |
| 4,713,051 A | 12/1987 | Steppe et al. |
| 4,758,238 A | 7/1988 | Sundblom et al. |
| 4,764,165 A | 8/1988 | Reimels et al. |
| 4,768,547 A | 9/1988 | Danby et al. |
| 4,790,726 A | 12/1988 | Balkau |
| 4,798,580 A | 1/1989 | Demeo et al. |
| 4,838,865 A | 6/1989 | Flank et al. |
| 4,854,825 A | 8/1989 | Bez |
| 4,861,332 A | 8/1989 | Parisi |
| 4,904,238 A | 2/1990 | Williams |
| 4,909,710 A | 3/1990 | Kaplan et al. |
| 4,909,713 A | 3/1990 | Finsterwald et al. |
| 4,921,477 A | 5/1990 | Davis |
| 4,923,375 A | 5/1990 | Ejlersen |
| 4,935,005 A | 6/1990 | Haines |
| 4,963,131 A | 10/1990 | Wortrich |
| 5,038,965 A | 8/1991 | Cater |
| 5,041,096 A | 8/1991 | Beuchat et al. |
| 5,044,902 A | 9/1991 | Malbec |
| 5,046,486 A | 9/1991 | Grulke et al. |
| 5,062,775 A | 11/1991 | Orth |
| 5,106,366 A | 4/1992 | Steppe |
| 5,106,367 A | 4/1992 | Ureche |
| 5,167,620 A | 12/1992 | Ureche |
| 5,185,002 A | 2/1993 | Venturini |
| 5,195,960 A | 3/1993 | Hossin et al. |
| 5,207,647 A | 5/1993 | Phelps |
| 5,257,917 A | 11/1993 | Minarik |
| 5,263,830 A | 11/1993 | Tseng |
| 5,267,956 A | 12/1993 | Beuchat |
| 5,273,517 A | 12/1993 | Barone et al. |
| 5,302,093 A | 4/1994 | Owens et al. |
| 5,316,440 A | 5/1994 | Kijima et al. |
| 5,342,181 A | 8/1994 | Schock |
| 5,350,357 A | 9/1994 | Kamen et al. |
| 5,364,342 A | 11/1994 | Beuchat et al. |
| 5,392,653 A | 2/1995 | Zanger et al. |
| 5,403,277 A | 4/1995 | Dodge et al. |
| 5,429,485 A | 7/1995 | Dodge |
| 5,429,601 A | 7/1995 | Appelbaum |
| 5,429,602 A | 7/1995 | Hauser |
| 5,443,370 A | 8/1995 | Wang |
| 5,460,490 A | 10/1995 | Carr et al. |
| 5,462,416 A | 10/1995 | Dennehey et al. |
| 5,470,312 A | 11/1995 | Zanger et al. |
| 5,476,448 A | 12/1995 | Urich |
| 5,484,239 A | 1/1996 | Chapman et al. |
| 5,487,747 A | 1/1996 | Stegmann et al. |
| 5,515,930 A | 5/1996 | Glaser |
| 5,518,378 A | 5/1996 | Neftel et al. |
| 5,533,976 A | 7/1996 | Zaleski et al. |
| 5,542,918 A | 8/1996 | Atkinson |
| 5,554,013 A | 9/1996 | Owens et al. |
| 5,575,632 A | 11/1996 | Morris et al. |
| 5,588,815 A | 12/1996 | Zaleski et al. |
| 5,616,118 A | 4/1997 | Ahmed |
| 5,630,711 A | 5/1997 | Luedtke et al. |
| 5,674,226 A | 10/1997 | Doherty |
| 5,688,112 A | 11/1997 | Garay |
| 5,697,910 A | 12/1997 | Cole et al. |
| 5,705,018 A | 1/1998 | Hartley |
| 5,709,539 A | 1/1998 | Hammer et al. |
| 5,712,543 A | 1/1998 | Sjostrom |
| 5,733,256 A | 3/1998 | Costin |
| 5,746,708 A | 5/1998 | Giesler et al. |
| 5,746,719 A | 5/1998 | Farra et al. |
| 5,759,017 A | 6/1998 | Patton et al. |
| 5,782,634 A | 7/1998 | Lingenhoele |
| 5,788,667 A | 8/1998 | Stoller |
| 5,810,765 A | 9/1998 | Oda |
| 5,827,218 A | 10/1998 | Nelson |
| 5,853,386 A | 12/1998 | Davis et al. |
| 5,879,363 A | 3/1999 | Urich |
| 5,897,300 A | 4/1999 | Luedtke |
| 5,897,524 A | 4/1999 | Wortrich et al. |
| 5,906,598 A | 5/1999 | Giesler et al. |
| 5,910,110 A | 6/1999 | Bastable |
| 5,927,956 A | 7/1999 | Lim et al. |
| 5,951,581 A | 9/1999 | Saadat et al. |
| 5,972,012 A | 10/1999 | Ream et al. |
| 5,989,212 A | 11/1999 | Cohen |
| 5,996,634 A | 12/1999 | Dennehey et al. |
| 5,997,499 A | 12/1999 | Cohen |
| 6,012,999 A | 1/2000 | Patterson |
| 6,042,586 A | 3/2000 | Kawano |
| 6,058,779 A | 5/2000 | Cole |
| 6,080,128 A | 6/2000 | Cohen |
| 6,109,895 A | 8/2000 | Ray et al. |
| 6,110,162 A | 8/2000 | Cohen |
| 6,117,149 A | 9/2000 | Sorensen et al. |
| 6,129,699 A | 10/2000 | Haight et al. |
| 6,179,805 B1 | 1/2001 | Cohen |
| 6,217,543 B1 | 4/2001 | Anis et al. |
| 6,241,700 B1 | 6/2001 | Leukanech |
| 6,270,326 B1 | 8/2001 | Kuriyama |
| 6,293,926 B1 | 9/2001 | Sorensen |
| 6,296,460 B1 | 10/2001 | Smith |
| 6,416,293 B1 | 7/2002 | Bouchard et al. |
| 6,491,661 B1 | 12/2002 | Boukhny et al. |
| 6,527,765 B2 | 3/2003 | Kelman et al. |
| 6,551,080 B2 | 4/2003 | Anderson et al. |
| 6,572,349 B2 | 6/2003 | Sorensen et al. |
| 6,599,277 B2 | 7/2003 | Neubert |
| 6,605,054 B2 | 8/2003 | Rockley |
| 6,655,934 B2 | 12/2003 | Sorensen |
| 6,689,146 B1 | 2/2004 | Himes |
| 6,723,065 B2 | 4/2004 | Kishimoto |
| 6,749,403 B2 | 6/2004 | Bryant et al. |
| 6,811,386 B2 | 11/2004 | Hedington et al. |
| 6,814,547 B2 | 11/2004 | Childers et al. |
| 6,868,987 B2 | 3/2005 | Hedington |
| 6,958,058 B1 | 10/2005 | Hunter, Sr. et al. |
| 6,962,488 B2 | 11/2005 | Davis et al. |
| 7,063,688 B2 | 6/2006 | Say |

(56) References Cited

U.S. PATENT DOCUMENTS

| | | |
|---|---|---|
| 7,070,574 B2 | 7/2006 | Jackson et al. |
| 7,144,383 B2 | 12/2006 | Arnett et al. |
| 7,150,607 B2 | 12/2006 | Pelmulder et al. |
| 7,238,164 B2 | 7/2007 | Childers et al. |
| 7,273,359 B2 | 9/2007 | Blight et al. |
| 7,276,060 B2 | 10/2007 | Madden |
| 7,393,189 B2 | 7/2008 | Davis et al. |
| 7,445,436 B2 | 11/2008 | Mittelstein et al. |
| 7,540,855 B2 | 6/2009 | Lumpkin et al. |
| 7,604,610 B2 | 10/2009 | Shener et al. |
| 7,632,080 B2 | 12/2009 | Tracey et al. |
| 7,645,127 B2 | 1/2010 | Hagen et al. |
| 7,695,242 B2 | 4/2010 | Fuller |
| 7,758,515 B2 | 7/2010 | Hibner |
| 7,775,780 B2 | 8/2010 | Hopkins et al. |
| 7,862,540 B2 | 1/2011 | Lind |
| 7,967,777 B2 | 6/2011 | Edwards et al. |
| 8,070,712 B2 | 12/2011 | Muri et al. |
| 8,087,909 B2 | 1/2012 | Shener |
| 8,162,633 B2 | 4/2012 | Edwards |
| 8,579,929 B2 | 11/2013 | Mackool |
| 8,617,106 B2 | 12/2013 | Zacharias |
| 9,132,034 B2 | 9/2015 | Dos Santos |
| 2001/0016706 A1 | 8/2001 | Leukanech et al. |
| 2002/0062105 A1 | 5/2002 | Tanner |
| 2002/0077587 A1 | 6/2002 | Boukhny et al. |
| 2003/0108429 A1 | 6/2003 | Angelini et al. |
| 2003/0199803 A1 | 10/2003 | Robinson et al. |
| 2004/0122381 A1 | 6/2004 | Arnold |
| 2004/0253129 A1 | 12/2004 | Sorensen et al. |
| 2005/0049539 A1 | 3/2005 | O'Hara, Jr. et al. |
| 2005/0070859 A1 | 3/2005 | Gal Aner |
| 2005/0100450 A1 | 5/2005 | Bryant et al. |
| 2005/0271531 A1 | 12/2005 | Chenvainu |
| 2006/0000925 A1 | 1/2006 | Maher et al. |
| 2006/0093989 A1 | 5/2006 | Hahn et al. |
| 2006/0110274 A1 | 5/2006 | Gottschalk |
| 2006/0122556 A1 | 6/2006 | Kumar et al. |
| 2006/0245964 A1 | 11/2006 | Koslov |
| 2006/0253194 A1 | 11/2006 | Dial |
| 2007/0078370 A1 | 4/2007 | Shener et al. |
| 2007/0078379 A1 | 4/2007 | Boukhny et al. |
| 2007/0100316 A1 | 5/2007 | Traxinger |
| 2007/0135760 A1 | 6/2007 | Williams |
| 2007/0217919 A1 | 9/2007 | Gordan et al. |
| 2007/0278155 A1 | 12/2007 | Lo |
| 2007/0287959 A1 | 12/2007 | Walter et al. |
| 2008/0097320 A1 | 4/2008 | Moore et al. |
| 2008/0112828 A1 | 5/2008 | Muri et al. |
| 2008/0114289 A1 | 5/2008 | Muri et al. |
| 2008/0114291 A1 | 5/2008 | Muri et al. |
| 2008/0114301 A1 | 5/2008 | Bandhauer et al. |
| 2008/0114311 A1 | 5/2008 | Muri et al. |
| 2008/0114312 A1 | 5/2008 | Muri et al. |
| 2008/0114372 A1 | 5/2008 | Edwards et al. |
| 2008/0200878 A1 | 8/2008 | Davis et al. |
| 2008/0220092 A1 | 9/2008 | DiPierro et al. |
| 2008/0240951 A1 | 10/2008 | Demash et al. |
| 2008/0247892 A1 | 10/2008 | Kawasumi |
| 2009/0012460 A1 | 1/2009 | Steck et al. |
| 2009/0035164 A1 | 2/2009 | Edwards |
| 2009/0060756 A1 | 3/2009 | Jones |
| 2009/0084718 A1 | 4/2009 | Prisco et al. |
| 2009/0246035 A1 | 10/2009 | Patzer |
| 2009/0299272 A1 | 12/2009 | Hopping et al. |
| 2009/0317271 A1 | 12/2009 | Gill et al. |
| 2010/0056979 A1 | 3/2010 | Gharib |
| 2010/0125257 A1 | 5/2010 | Perkins et al. |
| 2010/0130920 A1 | 5/2010 | Lo et al. |
| 2010/0130934 A1 | 5/2010 | Rochat |
| 2010/0145259 A1 | 6/2010 | Nash et al. |
| 2010/0191178 A1 | 7/2010 | Ross et al. |
| 2010/0228146 A1 | 9/2010 | Hibner |
| 2010/0241044 A1 | 9/2010 | Caleffi et al. |
| 2010/0280435 A1 | 11/2010 | Raney et al. |
| 2010/0286791 A1 | 11/2010 | Goldsmith |
| 2011/0092891 A1 | 4/2011 | Gerg et al. |
| 2011/0137231 A1 | 6/2011 | Sorensen et al. |
| 2011/0144567 A1 | 6/2011 | Sorensen et al. |
| 2011/0184374 A1 | 7/2011 | McDonell |
| 2012/0041358 A1 | 2/2012 | Mann et al. |
| 2012/0083728 A1 | 4/2012 | Sorensen et al. |
| 2013/0019968 A1* | 1/2013 | Liebing ............... A61M 1/101 |
| | | 137/565.01 |

FOREIGN PATENT DOCUMENTS

| | | |
|---|---|---|
| CA | 2743969 A1 | 3/2005 |
| CA | 2649867 C | 6/2010 |
| CN | 101023898 | 8/2007 |
| CN | 20091440 Y | 12/2007 |
| DE | 3809582 | 10/1989 |
| DE | 19749358 | 5/1998 |
| DE | 19711675 | 10/1998 |
| DE | 19856744 | 6/2000 |
| DE | 10034711 B4 | 2/2002 |
| DE | 10034711 A1 | 4/2006 |
| DE | 102007044790 | 4/2009 |
| EP | 0200448 A2 | 11/1986 |
| EP | 0320963 | 6/1989 |
| EP | 0362822 A2 | 4/1990 |
| EP | 518050 A1 | 12/1992 |
| EP | 518050 B1 | 7/1996 |
| EP | 0944404 A1 | 9/1999 |
| EP | 964711 B1 | 12/1999 |
| EP | 1140257 A1 | 10/2001 |
| EP | 1258260 A2 | 11/2002 |
| EP | 1810702 A1 | 7/2007 |
| EP | 2173404 A1 | 4/2010 |
| EP | 2365220 | 9/2011 |
| EP | 2509659 A1 | 10/2012 |
| FR | 2466641 | 4/1981 |
| FR | 2797190 | 2/2001 |
| GB | 2029514 | 3/1980 |
| GB | 2174763 A1 | 11/1986 |
| GB | 2190145 | 11/1987 |
| JP | 60001391 A | 1/1985 |
| JP | 63-290564 | 11/1988 |
| JP | 02070987 | 3/1990 |
| JP | H03-164586 | 7/1991 |
| JP | 2002-248117 | 9/2002 |
| JP | 3785643 | 6/2006 |
| JP | 2007-507636 | 3/2007 |
| JP | 2007-198382 | 8/2007 |
| JP | 2007-247646 | 9/2007 |
| JP | 2008-546501 | 12/2008 |
| RU | 2197277 | 1/2003 |
| RU | 2241887 | 12/2004 |
| SU | 1533696 A1 | 1/1990 |
| SU | 1590649 A1 | 9/1990 |
| WO | 9517597 | 6/1995 |
| WO | 98/18507 | 5/1998 |
| WO | 98/24495 | 6/1998 |
| WO | 99/38549 | 8/1999 |
| WO | 2000/22995 | 4/2000 |
| WO | 00/33898 | 6/2000 |
| WO | 00/53136 | 9/2000 |
| WO | 2003073969 A1 | 9/2003 |
| WO | 2005009511 A2 | 2/2005 |
| WO | 2005009511 A3 | 6/2005 |
| WO | 2008/131357 | 10/2008 |
| WO | 09/005900 | 1/2009 |
| WO | 09/146913 A2 | 12/2009 |
| WO | 09/146913 A3 | 2/2010 |
| WO | 10/061863 | 6/2010 |
| WO | 10/129128 | 11/2010 |
| WO | 2011/071775 | 6/2011 |
| WO | 2012048261 A2 | 4/2012 |
| WO | 2012048261 A3 | 6/2012 |

(56) References Cited

OTHER PUBLICATIONS

Written Opinion of the International Searching Authority, International Application No. PCT/US2010/058931, dated Feb. 1, 2011, 4 pages.
International Search Report for PCT/US2010/059032, filed Dec. 6, 2010, Publication No. 2011075332, Published Jun. 23, 2011, 2 pages.
Written Opinion of the International Searching Authority, International Application No. PCT/US2010/059032, dated Jan. 31, 2011, 5 pages.
(Citing Office Action), Non-Final Office Action, U.S. Appl. No. 12/637,886, dated Oct. 3, 2011, 11 pages.
Supplementary European Search Report for Application No. EP 10836456.3, Publication No. EP 2509659, Published Oct. 17, 2012, dated Mar. 20, 2013, 5 pages.
Supplementary European Search Report for Application No. EP 10838118.7, Publication No. EP2512554, Published Oct. 24, 2012, dated Apr. 15, 2013, 6 pages.
Milutinovic, et al., "Phacoemulsification Fluidics System Having a Single Pump Head," U.S. Appl. No. 12/818,682, filed Jun. 18, 2010, 28 pages.
International Searching Authority, Written Opinion of the International Searching Authority, International Application No. PCT/US2010/030168, dated Aug. 3, 2010, 8 pages.
International Search Report and Written Opinion of the International Searching Authority, International Application No. PCT/US2014/027271, filed Mar. 14, 2014, dated Jul. 28, 2014, 8 pages.
International Search Report and Written Opinion of the International Searching Authority, International Application No. PCT/US2014/027233, filed Mar. 14, 2014, dated Jul. 31, 2014, 10 pages.
International Search Report and Written Opinion of the International Searching Authority, International Application No. PCT/US2014/027307, filed Mar. 14, 2014, dated Jul. 30, 2014, 7 pages.
Sorensen, Gary, Phacoemulsification Hand Piece with Integrated Aspiration Pump, U.S. Appl. No. 13/325,549, filed Dec. 14, 2011, 18 pages.
http://www.advancedfluid.com/discflo/concepts.htm. Web archive dated Aug. 8, 2008, 3 pages.
Ovchinnikov et al., Acoustic Streaming of a Sharp Edge, Journal of Acoustical Society of America, 136 (1), Jul. 2014, pp. 22-29.
Barenblatt, G. I., Scaling, self-similarity, and intermediate asymptotics, 1966, pp. iv-15, Cambridge University Press, Cambridge.
Boluriaan, S. et al., Acoustic streaming: from Rayleigh to today, aeroacoustics, 2003, pp. 255-292, vol. 2, No. 3 & 4.
Extended European Search Report, Application No. 13863111.4, dated Jul. 14, 2015, 6 pgs.
Faraday, M., On a Peculiar Class of Acoustical Figures; and on Certain Forms Assumed by Groups of Particles upon Vibrating Elastic Surface, Philosophical Transactions of the Royal Society of London, 1831, pp. 299-340, vol. 121.
Holtsmark et. al., Boundary Layer Flow near a Cylindrical Obstacle in an Oscillating Incompressible Fluid, J. Acoust. Soc. Am., 1954, p. 102, 26.
Ingard, U. et al., Acoustic Circulation Effects and the Nonlinear Impedance of Orifices, The Journal of the Acoustical Society of America, Mar. 1950, pp. 211-218, vol. 22, No. 2.
International Preliminary Report on Patentability and Written Opinion issued for PCT/US2010/058931, dated Feb. 1, 2011, 5 pages.
International Preliminary Report on Patentability and Written Opinion of the International Searching Authority, Internatioinal Application No. PCT/2014/027271, dated Sep. 15, 2015, 6 pages.
International Preliminary Report on Patentability and Written Opinion of the International Searching Authority, International Application No. PCT/US2014/027307, dated Sep. 15, 2015, 5 pages.
International Preliminary Report on Patentability and Written Opinion of the International Searching Authority, issued for International Application No. PCT/US2010/059032, 6 pages.
International Preliminary Report on Patentability, PCT/US2013/064202, dated Jun. 16, 2015.
International Report on Patentability and Written Opinion of the International Searching Authority, International Application No. PCT/2014/027233, dated Sep. 15, 2015, 8 pages.
International Search Report and Written Opinion issued for PCT/US2014/064416 dated Feb. 18, 2015, 11 pages.
International Search Report and Written Opinion of the International Searching Authority, International Application No. PCT/2015/026293, dated Jul. 23, 2015, 10 pages.
International Search Report of the International Searching Authority, PCT/US2010/041786, dated Oct. 28, 2010, 5 pages.
International Searching Report of the International Searching Authority, PCT/US2015/037783, dated Sep. 28, 2015, 4 pages.
James, R. D. et al., A round turbulent jet produced by an oscillating diaphragm, Physics of Fluids, Sep. 1996, pp. 2484-2495, vol. 8, No. 9.
Kishimoto, Makoto, MD, OPESAVER—Super Irrigation System, Techniques in Opthalmology, 2006, 6 pages, vol. 4, Issue 1, Lippincott Williams & Wilkins, Shiga, Japan.
Landau, D. et al. (See for example), One-Dimensional Gas Flow, Fluid Dynamics, 1987. pp. 361-413, par. 10, problem 6, Pergamon Press, Oxford.
Lebedeva, I.V., Experimental study of acoustic streaming in the vicinity of orifices, Sov. Phys. Acoust., Jul.-Aug. 1980, pp. 331-333, vol. 26(4), Americal Institute of Physics.
Lighthill, J., Acoustic Streaming, Journal of Sound and Vibration, Jul. 1978, pp. 391-418, 61(3), Academic Press Inc., London.
Loh, B-G et al., Acoustic streaming induced by ultrasonic flexural vibrations and associated enhancement of convective heat transfer, J. Acoust. Soc. Am., Feb. 2002, pp. 875-883, vol. 111, No. 2.
Mednikov, E. P. et al., Experimental study of intense acoustic streaming, Sov. Phys. Acoust., Mar.-Apr. 1975, p. 152-154, vol. 21, No. 2.
Nyborg, W. L., Acoustic Streaming due to Attenuated Plane Waves, The Journal of the Acoustical Society of America, Sep. 30, 1952, pp. 68-75, vol. 25.
Nyborg, W. L., Acoustic Streaming near a Boundary, The Journal of the Acoustical Society of America, Dec. 16, 1957, pp. 329-339, vol. 30, No. 4.
Rayleigh, L., Theory of Sound, 1945, Par. 352, Dover Publications, New York.
Riley, N., Acoustic streaming about a cylinder in orthogonal beams, J. Fluid Mech., 1992, pp. 387-394, vol. 242.
Riley, N., Acoustic Streaming, Encyclopedia of Acoustics, 1997, pp. 321-327, vol. 1, ed M. J. Crocker, John Wiley & Sons, Inc., New York.
Riley, N., On a Sphere Oscillating in a Viscous Fluid, Quart. Journ. Mech. and Applied Math, Jan. 1966, pp. 461-472, vol. 19, Pt. 4.
Riley, N., Oscillatory Viscous Flows. Review and Extension J. Inst. Maths Applics, Jan. 30, 1967, pp. 419-434, 3.
Stuart, J. T., Double boundary layers in oscillatory viscous flow, J. Fluid Mech., 1966, pp. 673-687, vol. 24, part 4.
Taneda, S., Visualization of Steady Flows Induced by a Circular Cylinder Performing a Rotatory Oscillation about an Eccentric Axis, Journal of the Physical Society of Japan, Nov. 1980, pp. 2038-2041, vol. 49, No. 5.
Written Opinion of the International Searching Authority, PCT/US2009/057675, dated Mar. 25, 2011, 5 pages.
Written Opinion of the International Searching Authority, PCT/US2010/041786, dated Oct. 28, 2010, 7 pages.
Written Opinion of the International Searching Authority, PCT/US2015/037783, dated Sep. 28, 2015, 5 pages.
Zacharias, J. et al., Fluid dynamics, cavitation, and tip-to-issue interaction of longitudinal and torsional ultrasound modes during phacoemulsification, presentation at ASCRS meeting, 2010, pp. 611-616. Boston.

\* cited by examiner

ACTIVE ACOUSTIC STREAMING IN HAND PIECE FOR OCCLUSION SURGE MITIGATION

CROSS-REFERENCE TO RELATED APPLICATIONS

This application claims the benefit of 61/774,359, filed Mar. 7, 2013, the entire contents of which are incorporated herein by reference.

BACKGROUND

The present disclosure relates to phacoemulsification surgery and more particularly to acoustic streaming in a hand piece for occlusion surge mitigation during surgery.

TECHNICAL FIELD

The human eye functions to provide vision by transmitting light through a clear outer portion called the cornea, and focusing the image by way of a crystalline lens onto a retina. The quality of the focused image depends on many factors including the size and shape of the eye, and the transparency of the cornea and the lens. When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During a phacoemulsification procedure, a tip of a needle is inserted into the anterior segment of the eye through a small incision in the outer tissue of the eye. The surgeon brings the tip of the needle into contact with the lens of the eye, so that the vibrating tip fragments the lens. The resulting fragments are aspirated out of the eye through an interior bore of the needle, along with irrigation solution provided to the eye during the procedure.

A common complication during the phacoemulsification process arises from a blockage, or occlusion, of the lumen of the needle while aspirating material from the eye. As the irrigation fluid and emulsified tissue is aspirated away from the interior of the eye through the hollow needle, pieces of tissue that are larger than the diameter of the needle's bore may become lodged within the bore. While the needle is occluded, vacuum pressure builds up within the needle. An occlusion break is when the occlusion is removed, which results in a sudden surge of flow through the needle. This sudden flow results in a sudden reduction of pressure within the needle and the eye. The resulting drop in pressure in the anterior chamber of the eye when the occlusion is removed is known as post-occlusion surge. This post-occlusion surge can, in some cases, cause a relatively large quantity of fluid and tissue to be aspirated out of the eye too quickly, potentially causing the eye to collapse and/or causing the lens capsule to be torn.

There remains a need for improved phacoemulsification devices that reduce post-occlusion surge as well as maintain a stable intraocular pressure (IOP) throughout varying flow conditions. The present disclosure addresses one or more deficiencies in the prior art.

SUMMARY

In an exemplary aspect, the present disclosure is directed to an acoustic streaming arrangement operable to provide supplemental irrigation fluid flow to a surgical site. The acoustic streaming arrangement may include an irrigation conduit configured to carry an irrigation fluid to a surgical site, a flow generator having a sharp edge, and a driving device configured to selectively vibrate the flow generator to create a streaming fluid flow in a direction away from the sharp edge through the irrigation conduit.

According to another aspect, the present disclosure is directed to a surgical system, comprising an irrigation conduit configured to provide irrigating fluid to a surgical site, and an acoustic streaming arrangement configured to provide supplemental irrigation fluid to the surgical site.

According to a further aspect, the present disclosure is directed to a method comprising detecting a low pressure in a region with a pressure sensor during a surgical treatment, and activating an acoustic streaming arrangement to force fluid to the region and to stabilize the pressure.

The aspects of the disclosure may include one or more of the following features. The flow generator may include two nonparallel surfaces that form an angle. The two nonparallel surfaces may converge to form the sharp edge. The sharp edge may define an angle of 90 degrees or less. The driving device may be configured to vibrate the flow generator at a resonance frequency of the flow generator. The driving device may be one of a piezoelectric stack and a coil.

The surgical system may include a hand-held surgical instrument. The acoustic streaming arrangement may be disposed on the hand-held surgical instrument. The acoustic streaming arrangement may be in fluid communication with the irrigation conduit. The acoustic streaming arrangement may include a flow generator and a driving device configured to vibrate the flow generator to provide the supplemental irrigation fluid to the surgical site. The flow generator may include two nonparallel surfaces that form an angle. The two nonparallel surfaces may converge to form a sharp edge. The sharp edge may have an angle of 90 degrees or less. The sharp edge may be an extending edge. The flow generator may be disposed in the irrigation conduit. The surgical system may include an aspiration conduit configured to extend from the surgical site to carry fluid away from the surgical site. The surgical system may include an irrigation system operable to direct irrigating fluid to an eye for a phacoemulsification procedure. The irrigation conduit may form a part of the irrigation system. The surgical system may include an aspiration system operable to aspirate fluid from the eye during a phacoemulsification procedure. The surgical system may also include a phacoemulsification hand piece carrying the acoustic streaming arrangement. The hand piece may be connected to both the irrigation system and the aspiration system.

One or more of the aspects may also include one or more of the following features. A pressure may be detected in a region with a pressure sensor during a surgical treatment. Activating an acoustic streaming arrangement may include powering a driving device to induce vibration in a flow generator to force the fluid. The flow generator may be a wedge-shaped flow generator. The flow generator may be configured to create an acoustic stream from an edge.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

DETAILED DESCRIPTION OF THE PREFERRED EMBODIMENTS

Figure 1:
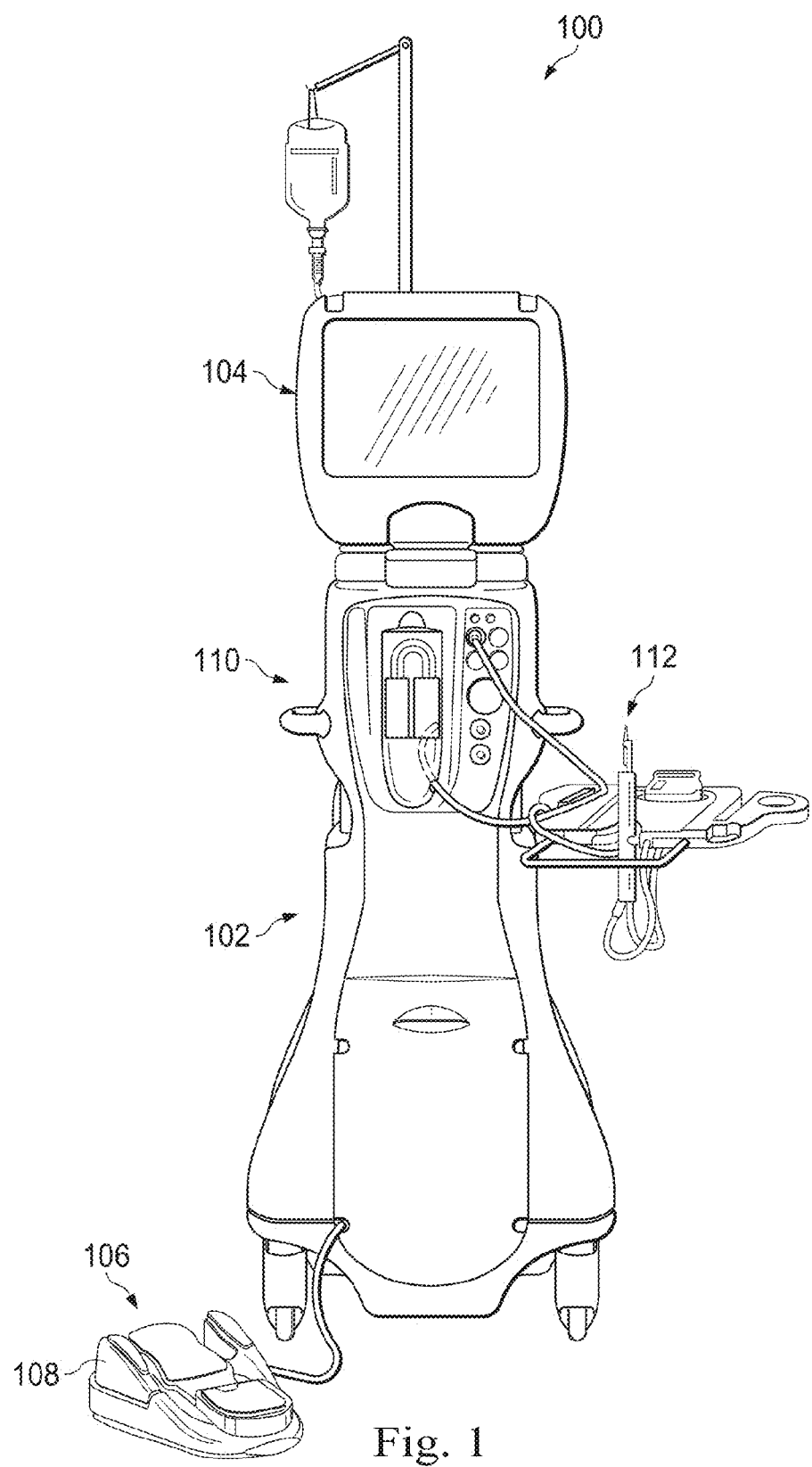
FIG. 1 shows an example phacoemulsification surgical console.

For the purposes of promoting an understanding of the principles of the present disclosure, reference will now be made to the example embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

The present disclosure relates generally to devices, systems, and methods for acoustic streaming of a fluid. More particularly, the disclosure relates to active acoustic streaming by vibrating a sharp edge in fluid to pump a small volume of the fluid into a surgical site during a surgical procedure. In one aspect, the disclosure relates to active acoustic streaming by ultrasonically vibrating a sharp edge on a surgical instrument to pump a small volume of fluid into the anterior chamber of eye to mitigate the effects of post-occlusion surge during a phacoemulsification procedure. In some aspects, the system uses the same driving device to both ultrasonically vibrate the sharp edge to create the fluid stream and to ultrasonically vibrate the cutting needle of a phacoemulsification hand piece. In some aspects, an active acoustic streaming chamber forms a part of the phacoemulsification hand piece and is configured and arranged to inject a fluid into an irrigation channel when a post-occlusion surge is detected in order to offset the drop in IOP.

Figure 2:
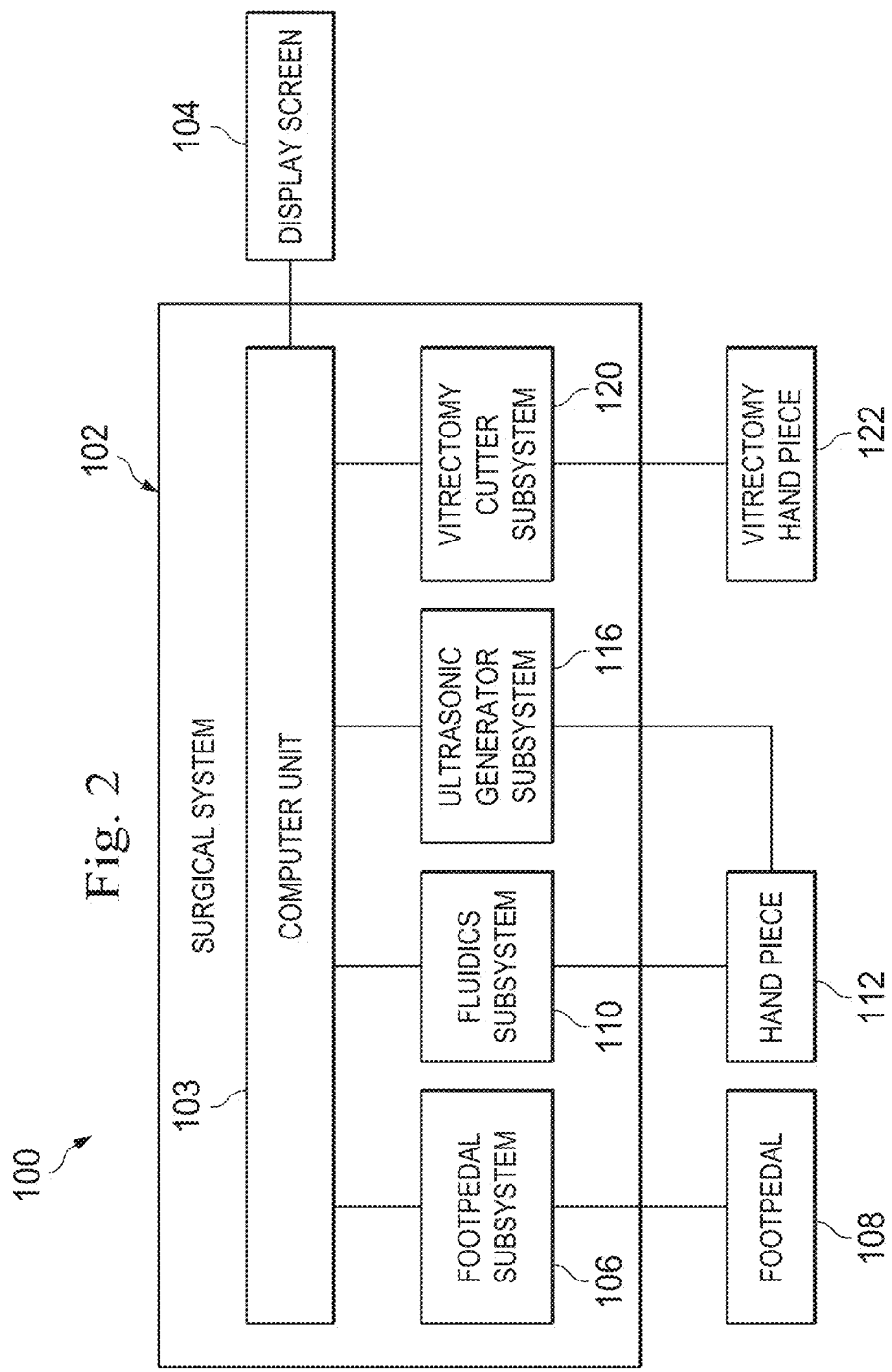
FIG. 2 is a block diagram of the phacoemulsification console of FIG. 1 showing various subsystems thereof.

FIG. 1 illustrates an exemplary emulsification surgical console, generally designated 100. FIG. 2 is a block diagram of the console 100 showing various subsystems that operate to perform a phacoemulsification procedure. The console 100 includes a base housing 102 with a computer unit 103 and an associated display screen 104. In some implementations, the display screen 4 is adapted to show data relating to operation and performance of the console 100 during an emulsification surgical procedure. The console 100 also includes a number of subsystems that may be used together to perform a phacoemulsification surgical procedure. For example, the subsystems may include one or more of a foot pedal subsystem 106 including, for example, a foot pedal 108, a fluidics subsystem 110 including a hand-held surgical instrument shown as hand piece 112, an ultrasonic generator subsystem 116 that is operable to cause a needle of the hand piece 112 to oscillate ultrasonically, and a pneumatic vitrectomy cutter subsystem 120 including a vitrectomy hand piece 122. These subsystems may overlap and cooperate to perform various aspects of a procedure or may be operable separately and/or independently from each other during one or more procedures. That is, some procedures may utilize one or more subsystems while excluding others.

Figure 3:
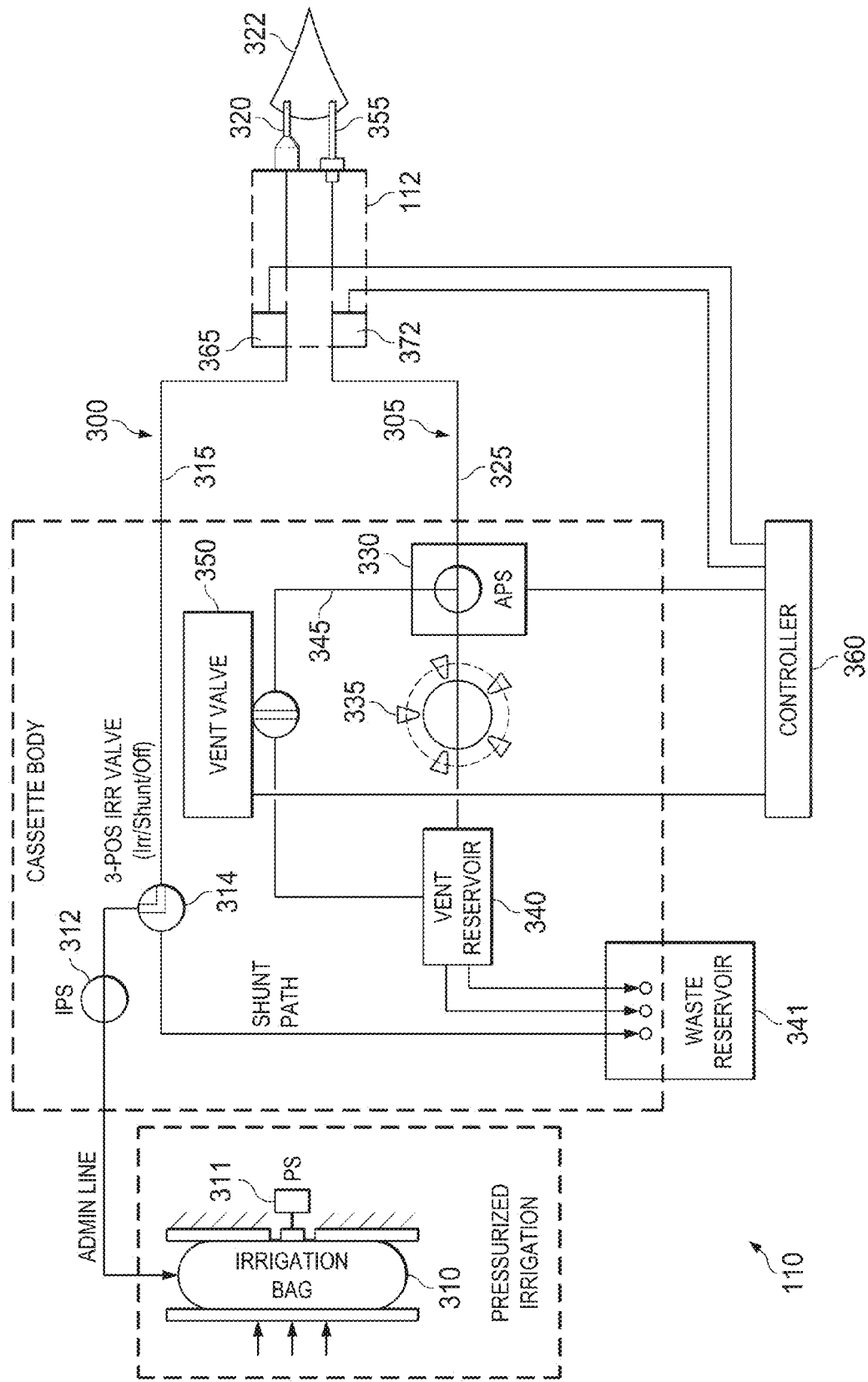
FIG. 3 is a schematic of an example fluidics subsystem that may be usable with the phacoemulsification surgical console of FIGS. 1 and 2.

FIG. 3 illustrates a schematic showing the fluidics subsystem 110 and the hand piece 112. The fluidics subsystem 110 includes an irrigation system 300 and an aspiration system 305 in fluid communication with the hand piece 112.

In some implementations, the irrigation system 300 includes an irrigation fluid source 310 and a flexible irrigation conduit 315 in fluid communication with a sleeve 320 located on the hand piece 112. The irrigation system 300 extends between the irrigation fluid source 310 and the hand piece 112, and carries fluid to the surgical site. For example, in FIG. 3, the surgical site is identified as an eye 322. In some implementations, the sterile fluid is a saline fluid; however, other fluids may be used.

In some instances, the irrigation fluid source 310 may be a mechanically pressurized fluid source. For example, in some implementations, the irrigation fluid source 310 may include a clamping pressure system as shown in FIG. 3. A clamping pressure system may include a fluid source contained in a flexible container disposed between rigid elements. The rigid element may be moveable relative to each other, and the rigid elements are operable to apply a selectable compressive force to the flexible container to produce a desired fluid pressure within the flexible container. A pressure sensor (PS) 311 may also be included. The PS 311 may sense a pressure of the irrigation fluid source 310. For example, in an implementation where the irrigation fluid source 311 is a flexible bag filled with irrigation fluid compressed by a rigid moveable element, the pressure sensor 311 may detect a pressure exerted by the bag. The sensed pressure from the PS 311 may be used to control a force applied to the irrigation fluid source 310 by the camping pressure system.

The irrigation system 300 may also include an irrigation fluid pressure sensor 312 disposed between the irrigation fluid source 310 and the hand piece 112. The irrigation fluid pressure sensor 312 is operable to sense a pressure of the irrigation fluid. A three-position valve 314 may also be included in the irrigation system 300. The three-position valve 314 is selectively moveable to provide fluid communication between a line extending from the irrigation fluid source 310 and a line extending to the hand piece 112. The valve 314 may be selectively positioned to provide communication between the irrigation fluid source 310 and a waste reservoir 341, described in more detail below. Thus, irrigation may be selectively provided from the irrigation fluid source 310 and the hand piece 112 or from the irrigation fluid source 310 to the waste reservoir 341. A position of the valve 314 may be selected by a user.

In other implementations, the irrigation fluid source 310 may include a gravity-fed fluid system. For example, in some instances, the irrigation fluid source 310 may include a fluid source suspended by an intravenous (IV) pole. Adjusting the elevation of the fluid source is operable to control the pressure head of the fluid within the fluid source and, consequently, a flow rate of the fluid through the irrigation conduit 315 to the surgical site. Other fluid sources also are contemplated.

The aspiration system 305 includes an aspiration conduit 325 located in fluid communication with the hand piece 112, an aspiration pressure sensor 330, a pump 335 interfacing with the aspiration conduit 325, and a vent reservoir 340. In some implementations, the pump 335 may be a dual segment elastomer pump operable to pump peristaltically. In other implementations, the pump 335 may be a single segment elastomer pump. In still other implementations, the pump 335 may have any number of elastomeric segments. In other instances, the pump 335 may be any suitable pump operable to pump fluid. In some implementations, the vent reservoir 340 may be a drain bag or an intersection of conduits. Other vent reservoirs also are contemplated. As can be seen, the aspiration system 305 extends from the surgical site (i.e., the eye 322 for the implementation illustrated in FIG. 3) to the vent reservoir 340 and ultimately on to the drainage or waste reservoir 341.

The pump 335 is operable to create a vacuum pressure within the aspiration conduit 325 between the pump 335 and the eye 322 to draw the aspiration fluid from the surgical site and into the vent reservoir 340. A bypass conduit 345 is also in fluid communication with the aspiration conduit 325 and the vent reservoir 340 and bypasses the pump 335. A vent valve 350 is located along the bypass conduit 345 and is operable to control the vacuum pressure within the aspiration conduit 325 by opening and closing, thereby respectively opening bypass conduit 345 to the atmosphere and isolating the bypass conduit 345 from the atmosphere.

Figure 4:
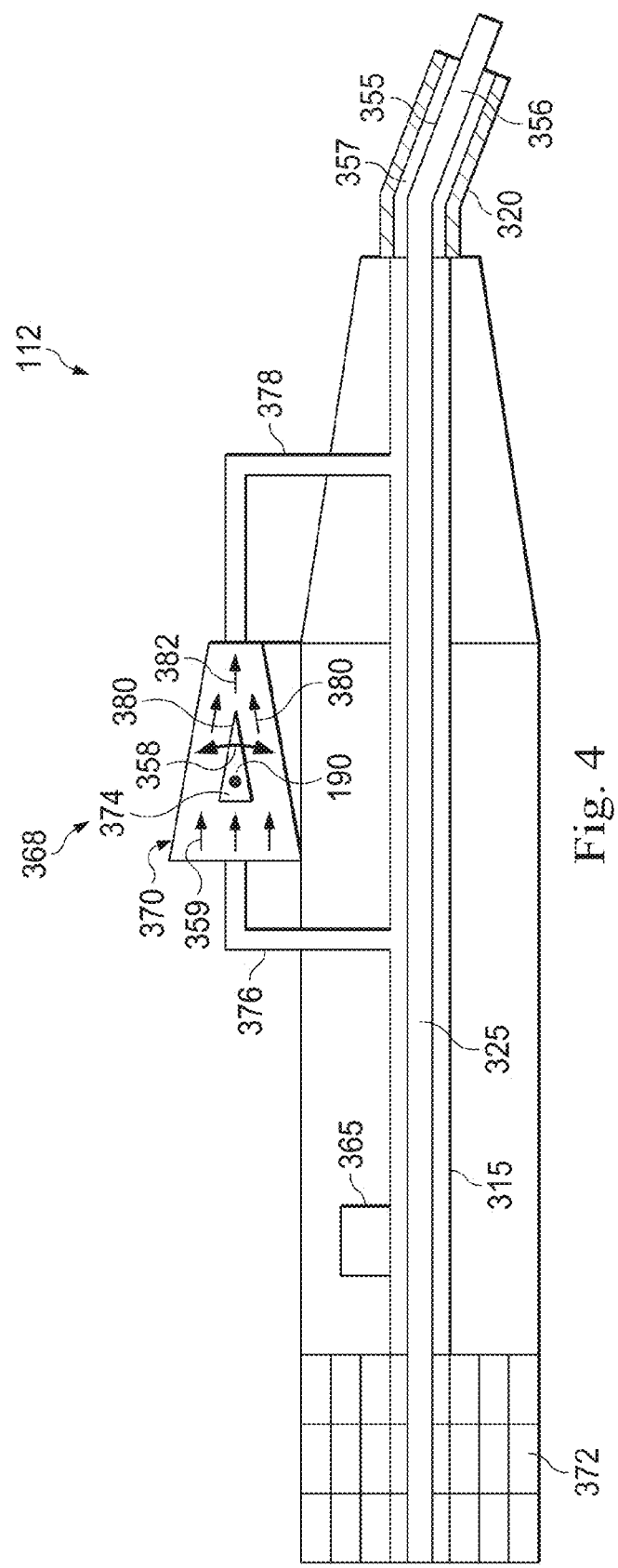
FIG. 4 is a schematic of an example hand piece that may be usable with the phacoemulsification surgical console of FIGS. 1 and 2.

The example hand piece 112 is shown schematically in FIG. 3, and is shown in greater detail in FIG. 4. In the example illustrated, the hand piece 112 includes a portion of the irrigation system 300 (e.g., a portion of irrigation conduit 315) and a portion of the aspiration system 305 (e.g., a portion of aspiration conduit 325). For explanatory purposes only, FIG. 3 shows the sleeve 320 and the needle 355 adjacent each other. However in use, the sleeve 320 and needle 355 are coaxial for insertion into the surgical site. That is, in some implementations, the needle 355 extends through the sleeve 320 in a coaxial arrangement.

FIG. 4 shows the example hand piece 112 in greater detail. Referring to FIG. 4, the hand piece 112 includes a portion of the irrigation conduit 315 and a portion of the aspiration conduit 325. The needle 355 extends through the sleeve 320 to define an annular space 357. The irrigation conduit 315 communicates with the annular space 357. The aspiration conduit 325 communicates with the needle 355. Irrigation fluid flows through the irrigation conduit 315, and through the annular space 357. Ultimately, the irrigation fluid is conducted to a surgical site, such as the eye 322 shown in FIG. 3. The aspiration conduit 325 transports fluid and emulsified particles from the lumen 356 of the needle 355 to the aspiration system 305 during the surgical procedure.

The hand piece 112 also includes a pressure sensor 365 and an acoustic streaming arrangement 368. The pressure sensor 365 is disposed in the hand piece 112 along the irrigation conduit 315. Although shown at the proximal end of the hand piece 112, in other embodiments, the pressure sensor 365 may be disposed at the distal end. In some instances, the pressure sensor 365 may be disposed proximate the sleeve 320. However, the pressure sensor 365 may be positioned at any location along the hand piece 112.

In some implementations, the pressure sensor 365 is an irrigation pressure sensor 365 located along the irrigation conduit 315 within the hand piece 112. The irrigation pressure sensor 365 is operable to detect an irrigation pressure within the irrigation conduit 315. In other implementations, the pressure sensor 365 is in fluid communication with the surgical site through a communication element. In some implementations, the communication element is an element other than the irrigation conduit 315. For example, the pressure sensor 365 may be disposed within its own separate tube or probe that is in communication with the surgical site. For example, in some instances, the separate tube or probe may be independent of the hand piece 112 but permits the pressure sensor 365 to be disposed within close proximity of the surgical site. In alternative embodiments, the pressure sensor 365 may be disposed within or on the sleeve 320 or elsewhere on the hand piece 112.

The acoustic streaming arrangement 368 includes an acoustic chamber 370 and a vibration-generating driving device 372. The acoustic chamber 370 is a fluid-filled chamber that includes a flow generator 374 and is disposed in communication with the irrigation conduit 315 via first and second shunt lines 376 and 378. In the example shown in FIG. 4, the first shunt line 376 extends from the irrigation conduit 315 at a proximal location thereof, and a second shunt line 378 extends from the irrigation conduit 315 at a distal location thereof. As will be explained below, in the event of a detected post-occlusion surge, the flow generator 374 generates fluid flow through the first and second shunt lines 376 and 378 to mitigate a drop in IOP. In some embodiments, the shunt line 376 connects the acoustic chamber 370 to a fluid reservoir separate from the irrigation conduit 315.

When activated, the flow generator 374 is configured to draw fluid through the first shunt line 376 and output fluid flow through the second shunt line 378. This fluid flow through the second shunt line 378 is introduced into the irrigation conduit 315, thereby increasing an overall fluid flow that is ultimately introduced into a surgical site, such as the eye 322 shown in FIG. 3. In some implementations, the flow generator 374 is a wedge-shaped blade. In some implementations, the flow generator 374 is a microscopic wedge-shaped blade. The flow generator 374 is arranged in the acoustic chamber 370 and is operable to vibrate back and forth about a pivot 190 in the direction of the arrow 358, as indicated in FIG. 4. In other implementations, the flow generator may be operable to laterally oscillate in a side-to-side motion.

Figure 5:
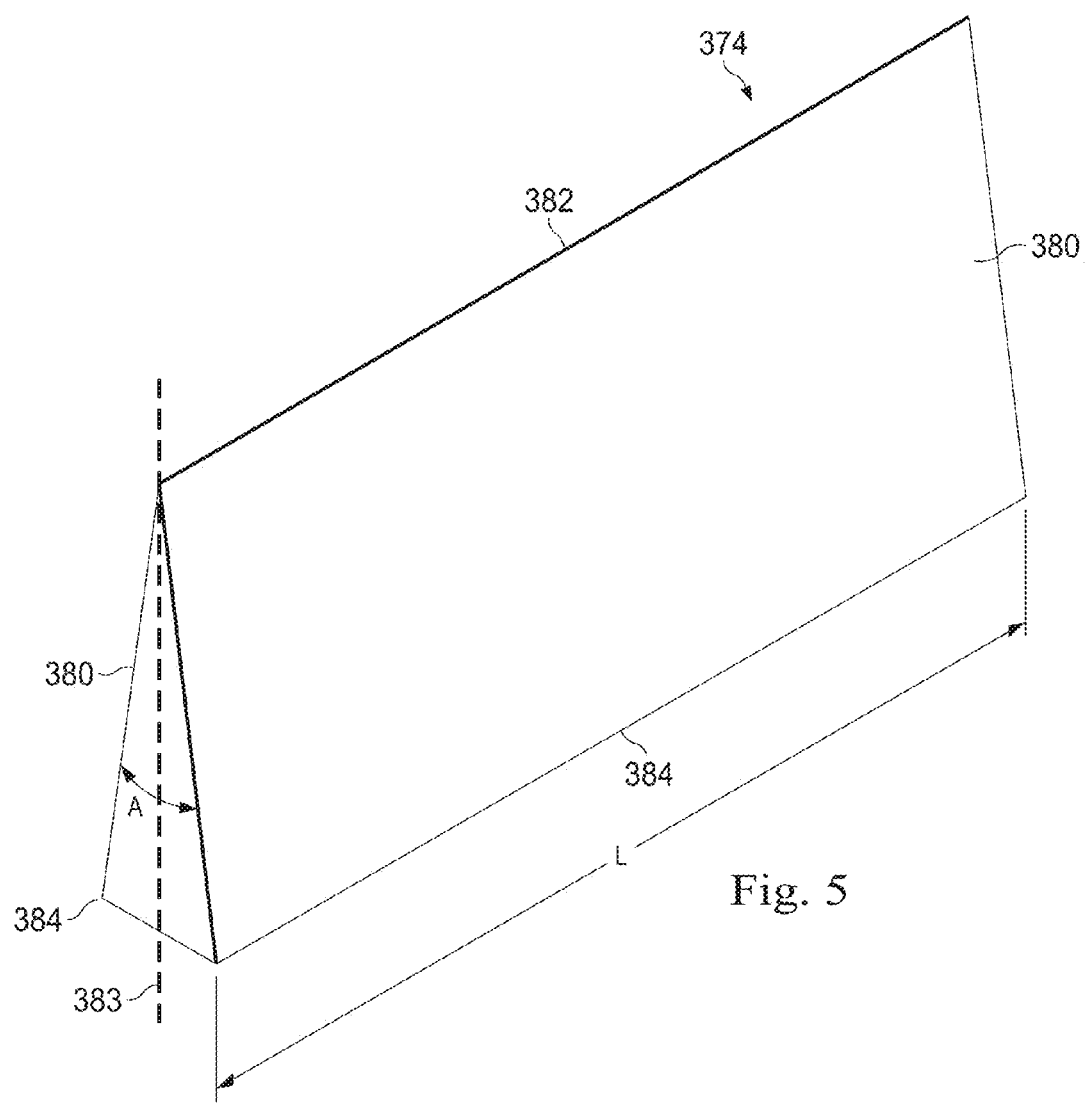
FIG. 5 shows an example fluid flow generator of the example hand piece of FIG. 4.

An example flow generator 374 is shown in greater detail in FIG. 5. The flow generator 374 has a length L that, in reference to FIG. 4, is in a direction normal to the plane of the drawing plane. With reference to FIGS. 4 and 5, the flow generator 374 includes angled, non-parallel sides 380 converging at a sharp edge 382, forming a wedge shape. In this example, the sharp edge 382 has a length L, as can be seen in FIG. 5. The two non-parallel sides 380 form an angle A at the sharp edge 382. In some instances, the angle A may be approximately 20 degrees. However, other angles are contemplated. For example, in some implementations, the angle A may be an angle between 10 and 90 degrees. In some implementations, the angle A may be an angle between 10 and 60 degrees, and, in still other implementations, angle A may be an angle between 15 and 30 degrees. In some instances, the angle A may be approximately 30 degrees.

Other ranges are also contemplated. The smaller the angle A, the higher the streaming velocities that may be achieved by the acoustic streaming arrangement 368. Here the sides 380 are symmetrically formed about an axis 383. In FIG. 3, the axis 383 aligns with a longitudinal axis of the acoustic chamber 370. In other implementations, the sides 380 may be asymmetrically formed about axis 383. That is, in some instances an angle formed between each of the sides 380 and the axis 383 may be unequal.

The amount of fluid pumped by the example acoustic streaming arrangement 368 may vary with the length L of the flow generator. For example, the flow generator 374 may have a lateral length L in the range of about 50 microns to 5 cm. In other embodiments, the lateral length L is in the range of about 100 microns to 2 cm. In some implementations, the flow generator 374 may be formed from a metal, such as steel or titanium. For example, the flow generator 374 may be formed from stainless steel. However, the scope of the disclosure is not so limited. Rather, the flow generator 374 may be formed of any suitable material. Further, in some particular implementations, the flow generator may be in the form of a steel blade and include an angle A of 20°. Additionally, in some implementations, the flow generator 374 may include rounded edges 384. Thus, in some instances, the flow generator 374 may include rounded edges 384 and an unrounded edge 382. In some instances, the flow generator 374 may form a tear-drop cross-sectional shape.

Referring again to FIG. 4, the flow generator 374 is disposed within the acoustic chamber 370, surrounded by fluid, and is operable to create an acoustic stream of fluid through the shunt lines 376 and 378. In some implementations, the flow generator 374 may be disposed directly in the irrigation line of a hand piece. In still other implementations, the flow generator 374 may be disposed within in the sleeve 320. The flow generator 374 may be attached to the walls of the acoustic chamber 370 or otherwise secured within the chamber 370.

The vibration-generating driving device 372 may be carried on the hand piece 112 and configured to provide an activating force to the flow generator 374 in the acoustic chamber 370. In other instances, the acoustic streaming arrangement 368 may be disposed within hand piece 112. The driving device 372 may be one or more piezoelectric crystals. The one or more piezoelectric crystals may form a piezoelectric crystal stack. When alternating current of a particular frequency is passed through the piezoelectric crystal stack, the stack vibrates at this frequency that may be used to mechanically drive the flow generator 374. In other instances, the driving device 372 may be an inductive device, such as a coil, and may be configured to generate a magnetic field that drives the flow generator 374. Other principles of vibration generation are also contemplated.

In some implementations, the driving device 372 may be or may form a part of other driving systems. For example, a hand piece that includes an ultrasonically powered driving device 372 may include an ultrasonic power source that provides ultrasonic power to both the acoustic streaming arrangement as well as to a phacoemulsification needle of the hand piece. Thus, a single device to generate ultrasonic vibrations may be used to power an acoustic streaming arrangement (e.g., vibrate a flow generator similar to flow generator 374) and ultrasonically vibrate a phacoemulsification needle, such as needle 355. The principle of vibration generation may be, for example, piezoelectric or inductive. In some embodiments, the ultrasonically vibrating phacoemulsification hand piece operates by driving the needle in a side-to-side movement. In other implementations, the ultrasonic vibrations may be used to produce both longitudinal and lateral (i.e. side-to-side) vibrations in the hand piece needle. This dual motion may result in a twisting action of the needle.

Figure 6:
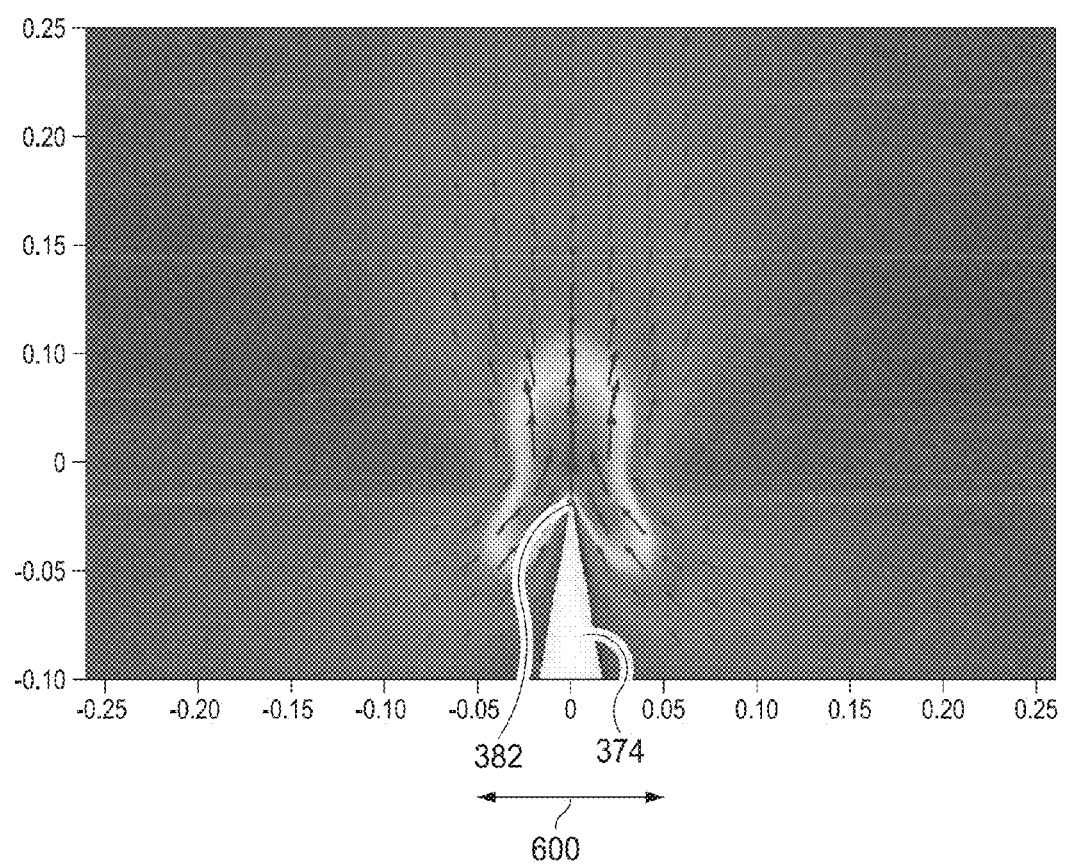
FIG. 6 is an illustration showing the principles of acoustic streaming jet flow obtained using the principles of the present disclosure.

FIG. 4 shows the flow generator 374 in an active condition or an acoustic streaming condition, as indicated by the vector arrows 358 representing flow in the acoustic chamber 370. Acoustic streaming is a steady streaming flow that is generated due to oscillatory motion of a sharp-edged body in a fluid. The steady streaming flow is represented in the drawing of FIG. 6. Anomalous jets of fluid are generated by and originate from the vibrating sharp tip or edge 382 of the microscopic wedge or blade forming the flow generator 374. Although example flow generators are described as microscopic, the scope of the disclosure encompasses flow generators that are macroscopic as well. In FIG. 6, the vectors represent the fluid velocity of to jets, and as can be seen, the velocity is much greater at the tip or sharp edge 382. The velocities of the jets can be as high as 2 m/s and are significantly higher than can be predicted by smooth edges vibrating laterally. The jets of fluid extend substantially perpendicular to the direction of lateral movement of the wedge in the directions of arrow 600 that is substantially parallel with the flow generator 374. In some implementations, a flow generator, such as flow generator 374, may be oscillated in its entirety in the directions of arrow 600. In other implementations, the flow generator may be pivotably oscillated about a point.

The anomalous streaming occurs at the sharp edge 382 of the wedge-shaped flow generator 374. The blade forming the flow generator 374 vibrates back and forth in the direction of arrow 600 and generates a strong microscopic current in the direction of the sharp edge 382 shown in the FIG. 6. Again, while a microscopic flow generator is described, the scope is not so limited. For example, in some instances, the flow generator may be macroscopic, and a resulting flow generated thereby may be a macroscopic flow. The spatial extent of this current may be influenced by the frequency of flow generator vibrations and viscosity of a fluid. For ultrasonic frequencies in water, the fluid flow around the flow generator 374 is localized to an area of several microns. The forces that produce such currents of flow are very strong and can easily overcome the surface tension of water and other fluids, which allows the use of this phenomenon to pump fluids like water and others. Thus, the acoustic streaming from the sharp edge 382 is typically highly localized at the sharp edge 382 with the dimensions that are much smaller than the acoustic wavelength. Because of the sharp edge 382 and the tapering sides 380 of the flow generator 374, the streaming is well localized at the sharp edge 382. Consequently, a shape of the flow generator 374 remote from the sharp edge 382 does not influence the generated flow. Thus, the geometry of the remainder of the flow generator 347 is largely irrelevant. For example, a shape of the flow generator 374 one tenth of a millimeter away from the sharp edge 382 or from 20 to 75 μm away from the sharp edge 382 does not affect the generated flow. In some instances, geometry of the flow generator 374 a distance in the range of 20 to 25 μm away from the sharp edge 382 may have any desired configuration, shape, or geometry. Thus, the geometry of the flow generator 374 remote from sharp edge 382 may be any desired geometry.

FIG. 6 also shows the vector field of the frequency-dependent fluid velocity. That is, FIG. 6 shows the vector field of fluid velocity that is dependent on the vibration frequency at which the flow generator is oscillated 374. As explained above, the vibration frequency may be an ultrasonic vibration frequency. In some examples, the fluid velocity is observed to be the highest just beyond (i.e., above as illustrated in FIG. 6) the sharp edge 382. The flow pattern consists of the stream directed vertically away from the sharp edge 382 which is fed by the streams coming from the sides. This pattern has proven to be universal for all angles of the sharp edge 382, fluid viscosities and frequencies of vibration.

To induce the streaming, the flow generator 374 may be vibrated at its resonance frequency. In some implementations, the flow generator 374 may be vibrated at its resonance frequency within a range of about 100 Hz to 10 MHz, for example. In some implementations, the vibration-generating driving device 372 may be driven at the frequency of 461 Hz, which may be resonance frequency of the flow generator 374 in water. For explanatory purposes, the acoustic motion introduces a boundary layer along the walls of the flow generator 374. The boundary layer is a low pressure acoustic force area, and it creates a path for fluid to enter. The fluid enters the acoustic force area along the sides of the flow generator 374 and is ejected at the sharp edge 382 driven by the centrifugal force. This results in the streaming pattern from the sharp edge 382.

Returning to FIG. 3, the fluidics subsystem 110 may also include a controller 360. The controller 360 is operable to communicate with the pressure sensor 365 located within the hand piece 112, the aspiration pressure sensor 330, the vent valve 350, and the driving device 372. The controller 360 may include a processor and memory that may include an executable program for operating the features of the fluidics subsystem. Thus, the controller 360 may be operable to control operation of the driving device 372 as well as to receive signals from the sensors 365 and 330. In some instances, the sensor 330 may be located in a surgical console and may be configured to measure aspiration pressure. Consequently, data sensed by the sensor 330 may be utilized to control an aspiration vacuum level. In some instances, the controller 360 is a PID controller configured to control the driving device 372 to mitigate pressure deviations, such as those that occur during post-occlusion surge. For example, the controller 360 may be operable to receive the signals from sensor 365 and/or sensor 330 and determine whether a post-occlusion surge has occurred. If a post occlusion surge is detected, the controller is operable to cause the acoustic streaming device to increase the flow rate of fluid provided to the eye 322.

In some implementations, the controller 360 may include one or more pre-established pressure thresholds establishing desired pressure limits. When the measured or detected pressure passes beyond these pre-established pressure thresholds, the controller 360 controls the driving device 372 to restore the pressure to a desired level. In some implementations, the pressure thresholds may be a function of IOP. The controller 360 may include a pressure threshold relating to the irrigation pressure as a representation of IOP. This may be, for example, a pressure threshold set below pressures at which the system operates under normal conditions (without occlusions or occlusion breaks). These pressure thresholds may be input by an operator or may be preset and stored during manufacturing or at any other time.

As explained above, the controller 360 may also receive information from the irrigation pressure sensor 365 and aspiration pressure sensor 330. The controller 360 is configured to control the operation of the driving device 372 based on the information received from the irrigation pressure sensor 365 and the aspiration pressure sensor 330. As indicated above, the pressure sensor 365 may be located on the hand piece 112 close to the surgical site. In some instances, the pressure sensor 365 may be disposed less than 12 inches from the surgical site. From its location in the hand piece 112, the irrigation pressure sensor 365 detects a fluid pressure representative of with the surgical site. The proximity to the eye 322 of sensor 365 enables quick detection of changes in pressure (e.g., as may occur during an occlusion break) and allows for a rapid response to a detected post-occlusion surge. For example, the rapid response may significantly diminish or eliminate post-occlusion surges. For example, in some instances, pressure changes may be detected as quickly as within 50 milliseconds of an occlusion break. Such a fast response time may enable the controller 360 to quickly provide a response to pressure deviations before IOP is negatively affected.

In operation, irrigation fluid is provided to a surgical site (e.g., eye 322 shown in FIG. 3) through the irrigation conduit 315. In the example shown in FIG. 4, the irrigation pressure sensor 365 is located along the irrigation conduit 315 to detect the pressure of the irrigation fluid within the irrigation conduit 315. The controller 360 continuously monitors the pressure of the irrigation fluid using the irrigation pressure sensor 365. If the pressure of the irrigation fluid drops below the selected pressure threshold, as may occur during a post-occlusion surge, the controller 360 activates the driving device 372. The driving device 372 in turn vibrates the flow generator 374 in the acoustic chamber 370. Because the acoustic chamber 370 is filled with fluid from the irrigation conduit 315 via, the first shunt line 376, activation of the flow generator 374 initiates an acoustic stream of fluid into the second shunt line 378 which results in a shot or burst of additional irrigation fluid being introduced to the eye 322. This shot of fluid may reduce or eliminate the drop in IOP that results from a post-occlusion surge. The acoustic chamber 370 is continuously filled with irrigation fluid from the irrigation conduit 315 via the first shunt line 376. Hence a fluid level within the acoustics chamber 370 is maintained.

In some implementations, the driving device 372 may continue to vibrate the flow generator 374 until the pressure, indicates the IOP 322 in the eye is stabilized. The irrigation pressure sensor 365 or the aspiration pressure sensor 330 may be used to detect whether IOP in the eye 322 has stabilized. The controller 360 may determine whether the IOP has stabilized by comparing signals received from the irrigation pressure sensor 365 and/or the aspiration pressure sensor corresponding to fluid pressure to a selected pressure threshold. As indicated above, there may be more than one pressure threshold. Also, one or more of the pressure thresholds may be entered by a user or stored in the controller 360 at the time of manufacturing.

In some implementations, the controller 360 may be operable to stop the driving device 372 without receipt of a measurement from the irrigation sensor 365 and/or the aspiration sensor 330. For example, in some instances, the driving device 372 may operate to provide supplementary irrigation fluid into the eye 322 for a selected period of time. The driving device 372 and, hence the flow generator 374, would be deactivated after a selected period of time. Thus, an increased flow rate of irrigation may be provided to the eye 322 or any other surgical site for a selected period of time and then discontinued. Accordingly, in such implementations, the controller 360 is operable to stop the driving device 372 after a preset period of time rather than for a period of time based on a detected pressure measurement.

Figure 7:
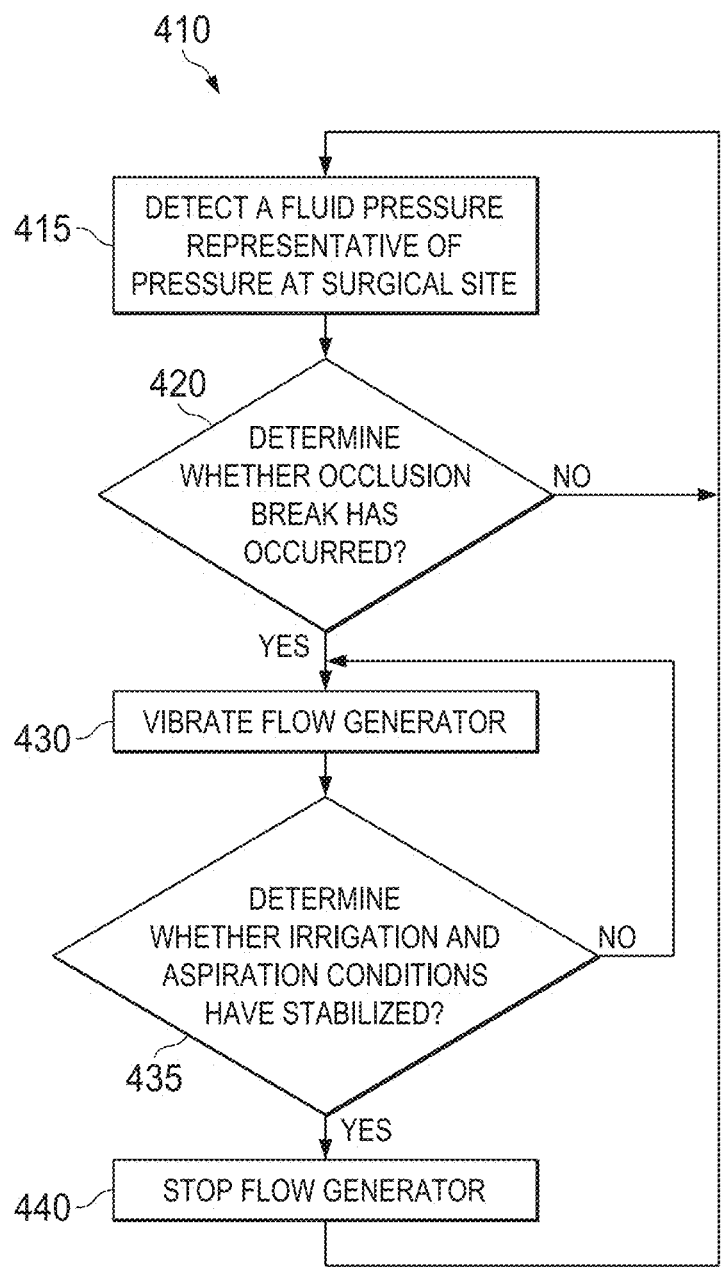
FIG. 7 is a flow chart of an example method of operating a fluidics system.

FIG. 7 illustrates an example method 410 for operating a fluidics system. For example, FIG. 7 illustrates a method that may be used to operate fluidics system 110. At step 415, a pressure sensor (e.g., the pressure sensor 365) detects a fluid pressure associated with the surgical site. For example, a pressure representative of IOP may be detected. The detected fluid pressure is communicated to a controller (e.g., the controller 360). Accordingly, the controller receives the detected pressure value. For example, the pressure sensor may be similar to pressure sensor 365. Thus, the pressure sensor may be an irrigation pressure sensor operable to detect pressure of an irrigation fluid within an irrigation conduit. In other instances, the pressure sensor may located on and/or detect a pressure of irrigation fluid within an irrigation sleeve, such as the irrigation sleeve 320. In still other instances, the pressure sensor may be otherwise disposed closely proximate to the surgical site and detect an irrigation fluid pressure proximate thereto.

At step 420, the controller determines whether an occlusion break, and associated post-occlusion surge, has occurred. For example, determination of whether a post-occlusion surge has occurred may be detected by comparing the fluid pressure measured by the pressure sensor to a selected pressure threshold to determine whether the pressure has dropped below the first pressure threshold. This drop in fluid pressure may be an indication of a pressure drop at the surgical site. For example, a drop in the measured fluid pressure below the selected pressure threshold may indicate a drop in IOP in the eye 322 below a desired pressure level. A drop in the detected fluid pressure below the selected pressure threshold may indicate a post-occlusion surge. For example, when the detected fluid pressure drops below the selected pressure threshold, the controller determines that a post-occlusion surge has occurred. However, if the pressure remains above or at the selected pressure threshold, then the controller determines that an occlusion break has not occurred. If the detected fluid pressure does not drop below the selected pressure threshold, normal operation. If a post-occlusion surge is detected, then the next step is step 430.

At the step 430, the controller operates a driving device to vibrate the flow generator in an acoustic chamber. For example, the controller 360 may be operable to operate the driving device 372. In turn, the driving device 372 may vibrate flow generator 374 in the acoustic chamber 370. Vibration of the flow generator is operable to inject an supplemental fluid flow through a shunt line, such as the shunt line 378, and into the surgical site. The supplemental fluid flowing from the acoustic chamber increases the flow of irrigation fluid into the eye. As a result, the impact of post-occlusion surge on the IOP is reduced.

At step 435, the controller determines whether the irrigation and aspiration conditions have stabilized. The controller may accomplish this, for example, by comparing the detected pressures from one or both of the irrigation pressure sensor and the aspiration pressure sensor with a second pressure threshold. The second pressure threshold may be the same with respect to both the detected pressures from the irrigation pressure sensor and the aspiration pressure sensor. Alternatively, a pressure threshold applied to the pressure detected by the irrigation pressure sensor may be different from a pressure threshold detected by the aspiration pressure sensor. The second pressure threshold may represent a limit of an acceptable or desired pressure. Accordingly, when the detected pressures satisfy the desired pressure threshold (e.g., the second pressure threshold), the system may be stabilized and the supplemental fluid from the acoustic streaming arrangement may be no longer necessary. For example, if the pressure detected by the irrigation pressure sensor and/or aspiration pressure sensor is above the second pressure threshold, the system may be determined to have stabilized. Consequently, if the detected pressure of the irrigation pressure sensor and/or aspiration pressure sensor is greater than or equal to the second pressure threshold applied respectively thereto, then the controller may deactivate the driving device to stop vibration of the flow generator at a step 440, and the system continues with normal operation at the step 425. Using this method, occlusion breaks are detected and the acoustic streaming arrangement may be used to mitigate the effects of a post-occlusion surge on IOP. As a result, the IOP during surgery may be maintained within a desired range, and fluctuations in IOP are reduced, thereby reducing the potential of increased turbulence and ocular tissue damage, such as damage to endothelial cells.

Figure 8:
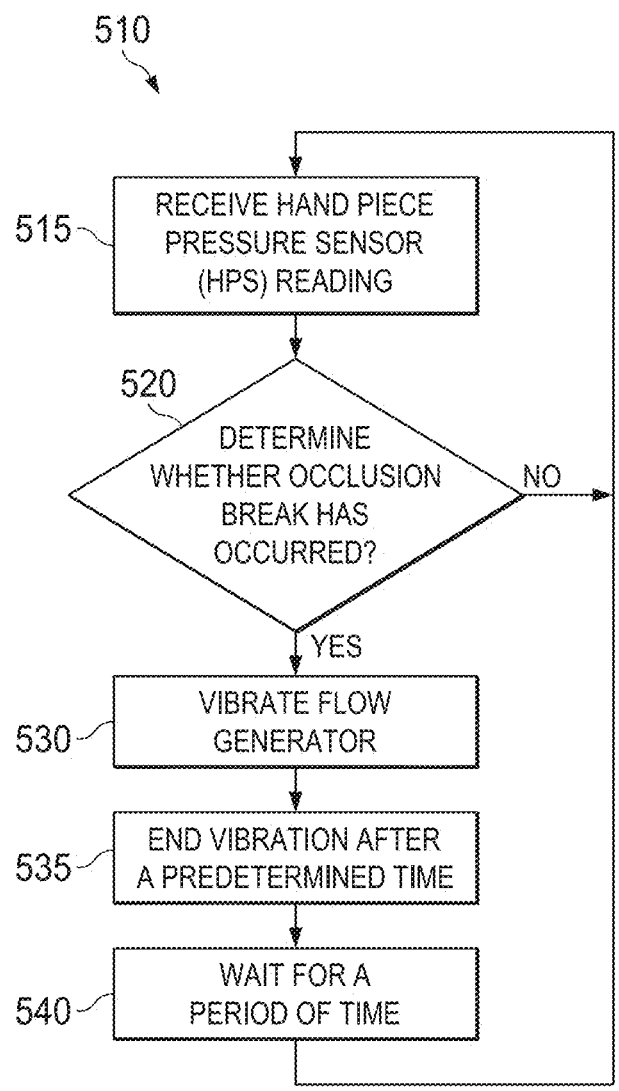
FIG. 8 is a flow chart of another example method of operating a fluidics system.

FIG. 8 illustrates another example method 510 for operating a fluidics system adapted to reduce fluctuations in IOP during an intraocular surgical procedure. Method 50 includes steps 515, 520, and 530 that may be substantially similar to the steps 415, 420, 425 and 430 of the method 410, respectively, and therefore will not be discussed in detail. At step 535 of method 510, the controller may stop operation of the driving device and, hence, vibration of the flow generator, after a first selected time. At step 540, the system waits for a second selected period of time before continuing with normal operation at the step 525. The second selected period of time is selected to permit the system to normalize after use driving device and flow generator and associated supplemental fluid flow. Normal operation may be resumed at step 515 after the second selected period of time has elapsed.

While a phacoemulsification hand piece is shown and described, it should be apparent that the acoustic streaming arrangement may be used in any irrigating surgical instrument.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An acoustic streaming arrangement operable to provide supplemental irrigation fluid flow to a surgical site, the acoustic streaming arrangement comprising:
   an irrigation conduit configured to carry an irrigation fluid to a surgical site;
   an acoustic chamber in fluid communication with the irrigation conduit via a first shunt line at a first end of the acoustic chamber and a second shunt line at a second end of the acoustic chamber;
   a flow generator disposed in the acoustic chamber, the flow generator having a sharp edge; and
   a driving device configured to selectively vibrate the flow generator to create a streaming fluid flow in a direction away from the sharp edge through the irrigation conduit.

2. The acoustic streaming arrangement of claim 1, wherein the flow generator comprises two nonparallel surfaces forming an angle.

3. The acoustic streaming arrangement of claim 2, wherein the two nonparallel surfaces converge to form the sharp edge.

4. The acoustic streaming arrangement of claim 2, wherein the sharp edge defines an angle of 90 degrees or less.

5. The acoustic streaming arrangement of claim 1, wherein the driving device is configured to vibrate the flow generator at a resonance frequency of the flow generator.

6. The acoustic streaming arrangement of claim 1, wherein the driving device is one of a piezoelectric stack and a coil.

7. A surgical system, comprising:
  an irrigation conduit configured to provide irrigation fluid to a surgical site; and
  an acoustic streaming arrangement disposed in an acoustic chamber adjacent to and in fluid communication with the irrigation conduit;
  a supplemental fluid flow generated by the acoustic streaming arrangement and introduced into the irrigation conduit via a shunt line, the supplemental fluid flow provided to the surgical site via the irrigation conduit.

8. The surgical system of claim 7, further comprising a hand-held surgical instrument, the acoustic streaming arrangement being disposed on the hand-held surgical instrument.

9. The surgical system of claim 7, further comprising a driving device,
  wherein the acoustic streaming arrangement comprises a flow generator, and
  wherein the driving device is configured to vibrate the flow generator to provide the supplemental fluid flow to the surgical site.

10. The surgical system of claim 9, wherein the flow generator comprises two nonparallel surfaces forming an angle.

11. The surgical system of claim 10, wherein the two nonparallel surfaces converge to form a sharp edge.

12. The surgical system of claim 11, wherein the sharp edge defines an angle of 90 degrees or less.

13. The surgical system of claim 7, further comprising an aspiration conduit configured to extend from the surgical site and operable to conduct fluid away from the surgical site.

14. The surgical system of claim 7, further comprising:
  an irrigation system operable to direct irrigating fluid to an eye for a phacoemulsification procedure, the irrigation conduit being a part of the irrigation system;
  an aspiration system operable to aspirate fluid from the eye during a phacoemulsification procedure; and
  a phacoemulsification hand piece carrying the acoustic streaming arrangement, the hand piece being connected to both the irrigation system and the aspiration system.

* * * * *